US006692537B1

(12) United States Patent
de la Mettrie et al.

(10) Patent No.: US 6,692,537 B1
(45) Date of Patent: Feb. 17, 2004

(54) OXIDIZING COMPOSITION AND USE FOR DYEING, PERMANENTLY SETTING OR BLEACHING KERATIN FIBRES

(75) Inventors: Roland de la Mettrie, Le Vésinet (FR); Jean Cotteret, Verneuil sur Seine (FR); Arnaud de Labbey, Aulnay sous Bois (FR); Mireille Maubru, Chatou (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/319,200

(22) PCT Filed: Sep. 22, 1998

(86) PCT No.: PCT/FR98/02020

§ 371 (c)(1),
(2), (4) Date: Jun. 30, 1999

(87) PCT Pub. No.: WO99/17723

PCT Pub. Date: Apr. 15, 1999

(30) Foreign Application Priority Data

Oct. 3, 1997 (FR) .............................................. 97 12362

(51) Int. Cl.[7] .............................. C09B 67/00; A61K 7/13
(52) U.S. Cl. .................... 8/401; 8/405; 8/428; 8/557; 8/558; 424/70.1; 424/70.2; 424/70.11; 424/70.16
(58) Field of Search ........................... 8/401, 557, 558, 8/405, 428; 424/70.11, 70.2, 70.16, 70.1

(56) References Cited

U.S. PATENT DOCUMENTS

| | | | |
|---|---|---|---|
| 3,907,799 A | | 9/1975 | O'Brien et al. ........ 260/256.4 F |
| 4,394,520 A | * | 7/1983 | Kalopissis ................... 562/557 |
| 4,961,925 A | | 10/1990 | Tsujino et al. ................. 424/71 |
| 5,616,746 A | * | 4/1997 | Mahieu et al. ................. 554/66 |
| 6,001,376 A | * | 12/1999 | Mahieu et al. ............... 424/401 |
| 6,027,719 A | * | 2/2000 | Tomura et al. ........... 424/78.02 |

FOREIGN PATENT DOCUMENTS

| | | |
|---|---|---|
| DE | 23 59 399 | 6/1975 |
| DE | 3843892 | 6/1990 |
| DE | 41 33 957 | 4/1993 |
| DE | 195 43 988 | 5/1997 |
| DE | 195 47 991 | 6/1997 |
| EP | 0 310 675 | 4/1989 |
| EP | 0 550 106 A1 | 7/1993 |
| EP | 0 628 559 | 12/1994 |
| EP | 0 716 846 | 6/1996 |
| EP | 0 766 958 | 4/1997 |
| EP | 0 795 313 | 9/1997 |
| FR | 2 586 913 | 3/1987 |
| FR | 2 733 749 | 11/1996 |
| GB | 1 026 978 | 4/1966 |
| GB | 1 153 196 | 5/1969 |
| JP | 63-169571 | 7/1988 |
| JP | 9-110659 | 4/1997 |
| WO | WO 92/05764 | 4/1992 |
| WO | WO 94/08969 | 4/1994 |
| WO | WO 94/08970 | 4/1994 |
| WO | WO 96/15765 | 5/1996 |
| WO | WO 97/24105 | 7/1997 |

OTHER PUBLICATIONS

Vishnu J. Ram et al., "Synthesis of bioisosteric pyrazolo[1,5–a]pyrimidines as leishmanicides", Indian Journal of Chemistry, vol. 34B, Jun. 1995, pp. 514–520.
Nadia S. Ibraham et al., "Studies on 3,5–Diaminopyrazoles: Synthesis of New Polyfunctionally Substituted Pyrazoloazines and Pyrazoloazoles", Archiv der Pharmazie, vol. 320, No. 3, Mar. 1987, pp. 240–246.
Robert H. Springer et al., "Synthesis and Enzymic Activity of 6–Carbethoxy– and 6–Ethoxy–3,7–disubstituted–pyrazolo[1,5–α]pyrimidines and Related Derivatives as Adenosine Cyclic 3',5'–Phosphate Phosphodiesterase Inhibitors", Journal of Medicinal Chemistry, vol. 25, No. 3, 1982, pp. 235–242.
Thomas Novinson et al., "Synthesis and Antifungal Properties of Certain 7–Alkylaminopyrazolo[1,5–a]pyrimidines", Journal of Medicinal Chemistry, vol. 20, No. 2, 1977, pp. 296–299.
Alexander McKillop et al., "Reaction of Hydrazine with β–Aminocrotononitrile: Synthesis of 2,7–dimethyl–5–aminopyrazolo[1,5–a]pyrimidine", Heterocycles, vol. 6, Nos. 9, 10, 1977, pp. 1355–1360.
Koji Saito et al., "The Reaction of Ethyl Ethoxymethylenecyanoacetate with Its Hydrazino Derivatives", Bulletin of the Chemical Society of Japan, vol. 47, No. 2, 1974, pp. 476–480.
Ermitas Alcade et al., "Etude de la réaction du β–aminocrotonitrile et du α–formyl phénylacétonitrile avec l'hydrazine: synthèse d'amino–7 pyrazolo[1,5–a]pyrimidines", Journal of Heterocyclic Chemistry, vol. 11, No. 3, Jun. 1974, pp. 423–429.
English language Derwent Abstract of DE 23 59 399.
English language Derwent Abstract of DE 38 43 892.
English language Derwent Abstract of DE 41 33 957.
English language Derwent Abstract of DE 195 43 988.
English language Derwent Abstract of DE 195 47 991.
English language Derwent Abstract of EP 0 766 958.
English language Derwent Abstract of EP 0 795 313.
English language Derwent Abstract of FR 2 586 913.
English language Derwent Abstract of FR 2 733 749.
English language Derwent Abstract of JP 63–169571.
English language Derwent Abstract of JP 9–110659.

\* cited by examiner

*Primary Examiner*—Yogendra N Gupta
*Assistant Examiner*—D G Hamlin
(74) *Attorney, Agent, or Firm*—Finnegan, Henderson, Farabow, Garrett & Dunner, LLP

(57) ABSTRACT

The present application relates to a cosmetic composition intended for treating keratin fibers, comprising, in a support which is suitable for keratin fibers:

(a) at least one enzyme of 2-electron oxidoreductase type in the presence of at least one donor for the said enzyme;
(b) at least one nonionic fatty sucronamide;
    as well as to processes for treating keratin fibers, in particular processes for dyeing, permanently reshaping or bleaching the hair, using this composition.

61 Claims, No Drawings

OXIDIZING COMPOSITION AND USE FOR DYEING, PERMANENTLY SETTING OR BLEACHING KERATIN FIBRES

The present invention relates to an oxidizing composition intended for treating keratin fibres, comprising at least one enzyme of 2-electron oxidoreductase type in the presence of at least one donor for the said enzyme and at least one nonionic fatty sucronamide, as well as to its uses for dyeing, for permanently reshaping or for bleaching keratin fibres, in particular human hair.

It is known to dye keratin fibres, and in particular human hair, with dye compositions containing oxidation dye precursors, in particular para-phenylenediamines, ortho- or para-aminophenols and heterocyclic bases which are generally referred to as oxidation bases. Oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with couplers or colour modifiers, the latter being chosen in particular from aromatic meta-diamines, meta-aminophenols, meta-diphenols and certain heterocyclic compounds.

The variety of compounds used as regards the oxidation bases and the couplers allows a wide range of colours to be obtained.

The so-called "permanent" coloration obtained by means of these oxidation dyes must moreover satisfy a certain number of requirements. Thus it must have no toxicological drawbacks, it must be able to give shades of the desired intensity and it must be able to withstand external agents (light, bad weather, washing, permanent-waving, perspiration, rubbing).

The dyes must also be able to cover white hair and, lastly, they must be as unselective as possible, i.e. they must give the smallest possible colour differences along the same length of keratin fibre, which may in fact be differently sensitized (i.e. damaged) between its tip and its root.

The oxidation dyeing of keratin fibres is generally carried out in alkaline medium, in the presence of hydrogen peroxide. However, the use of alkaline media in the presence of hydrogen peroxide has the drawback of causing appreciable degradation of the fibres, as well as considerable bleaching of the keratin fibres, which is not always desirable.

The oxidation dyeing of keratin fibres can also be carried out using oxidizing systems other than hydrogen peroxide, such as enzymatic systems. Thus, it has already been proposed to dye keratin fibres, in particular in patent application EP-A-0,310,675, with compositions comprising an oxidation dye precursor in combination with enzymes such as pyranose oxidase, glucose oxidase or uricase, in the presence of a donor for the said enzymes. Although being used under conditions which do not result in degradation of the keratin fibres which is comparable to that caused by the dyes used in the presence of hydrogen peroxide, these dye formulations nevertheless lead to colorations which are still insufficient, both as regards the homogeneity of the colour distributed along the fibre ("unison") and as regards the chromaticity (luminosity), the dyeing power and the resistance to the various aggressive factors to which the hair may be subjected.

It is known that the most common technique for obtaining a permanent reshaping of the hair consists, in a first stage, in opening the keratin-S-S-disulphide (cysteine) bonds using a composition containing a suitable reducing agent (reduction step) followed, after having rinsed the hair thus treated, by reconstituting, in a second stage, the said disulphide bonds by applying to the hair, which has been placed under tension beforehand (curlers and the like), an oxidizing composition (oxidation step, also known as the fixing step) so as finally to give to the hair the desired shape. This technique thus makes it equally possible either to make the hair wavy or to straighten it or to remove its curliness. The new shape given to the hair by a chemical treatment such as above is remarkably long-lasting and in particular resists the action of washing with water or shampoos, as opposed to simple standard techniques for temporary reshaping, such as hairsetting.

The reducing compositions which may be used in order to carry out the first step of a permanent-waving operation generally contain, as reducing agents, sulphites, bisulphites, alkylphosphines or, preferably, thiols. Among the thiols, those commonly used are cysteine and the various derivatives thereof, cysteamine and the derivatives thereof, thiolactic acid or thioglycolic acid, the salts thereof and the esters thereof, in particular glyceryl thioglycolate.

As regards the oxidizing compositions needed to carry out the fixing step, use is usually made in practice of compositions based on aqueous hydrogen peroxide, sodium bromate or persalts such as sodium perborate, which have the drawback of being liable to damage the hair.

The problem of the technique of the permanent-waving operations known to date is that their application to the hair induces long-term adverse changes in the quality of the hair. The essential causes of these adverse changes in the quality of the hair are a reduction in its cosmetic properties, such as its sheen and its feel, and degradation of its mechanical properties, more particularly degradation of its mechanical strength due to swelling of the keratin fibres during the rinsing between the reduction step and the oxidation step, which can also be reflected by an increase in its porosity. The hair is weakened and can become brittle during subsequent treatments such as blow-drying.

The same problem of adverse changes in keratin fibres is encountered during processes for bleaching the hair.

It is known that the permanent reshaping or bleaching of keratin fibres can also be carried out under milder conditions using oxidizing systems other than hydrogen peroxide, such as enzymatic systems. Thus, processes for the permanent reshaping or bleaching of keratin fibres have already been proposed, in particular in patent application EP-A-0,310,675, with compositions comprising an enzyme such as pyranose oxidase, glucose oxidase or uricase, in the presence of a donor for the said enzyme. Although being used under conditions which do not result in degradation of the keratin fibres which is comparable to that caused by conventional permanent-waving or bleaching processes, these oxidizing formulations nevertheless lead to results which are still insufficient, as regards the curl hold over time, as regards the compatibility of permanent-waved or bleached hair with subsequent treatments, as regards the degradation of the mechanical properties of the permanent-waved hair, in particular the reduction of the porosity of the hair, and as regards the reduction of the cosmetic properties such as the feel, or alternatively as regards the uniformity of the bleaching along the keratin fibres.

The aim of the present invention is to solve the problems mentioned above.

The Applicant has discovered, surprisingly, novel compositions containing, as oxidizing system, at least one enzyme of 2-electron oxidoreductase type in the presence of at least one donor for the said enzyme and at least one nonionic fatty sucronamide, which can constitute, in the presence of oxidation dye precursors and optionally couplers, ready-to-use dye formulations which lead to more homogeneous, more intense and more chromatic colorations without giving rise to any significant degradation, these colorations being relatively unselective and showing good resistance to the various aggressive factors to which the hair may be subjected.

The Applicant has also discovered, unexpectedly, that the use, in a process for the permanent reshaping of keratin fibres, of an oxidizing composition containing, as oxidizing system, at least one enzyme of 2-electron oxidoreductase type in the presence of at least one donor for the said enzyme and at least one nonionic fatty sucronamide, makes it possible to solve the technical problems mentioned above. In particular, this type of oxidizing composition improves the curl hold obtained over time, substantially reduces the porosity of permanent-waved hair and improves the compatibility of permanent-waved hair with respect to subsequent treatments.

The Applicant has also discovered, surprisingly, that the use, in a process for bleaching keratin fibres, of an oxidizing composition containing, as oxidizing system, at least one enzyme of 2-electron oxidoreductase type in the presence of at least one donor for the said enzyme and at least one nonionic fatty sucronamide, makes it possible to solve the technical problems mentioned above, in particular to improve the compatibility of bleached hair with respect to subsequent treatments. This type of oxidizing composition gives a more uniform bleaching effect on the hair and improves the cosmetic properties, such as the feel.

These discoveries form the basis of the present invention.

The subject of the present invention is thus, firstly, a cosmetic and/or dermatological composition intended for treating keratin fibres, in particular human keratin fibres and more particularly human hair, comprising, in a support which is suitable for keratin fibres:
 (a) at least one enzyme of 2-electron oxidoreductase type in the presence of at least one donor for the said enzyme,
 (b) at least one nonionic fatty sucronamide.

The 2-electron oxidoreductase(s) used in the oxidizing compositions in accordance with the invention can be chosen in particular from pyranose oxidases, glucose oxidases, glycerol oxidases, lactate oxidases, pyruvate oxidases and uricases.

According to the invention, the 2-electron oxidoreductase is preferably chosen from uricases of animal, microbiological or biotechnoloaical origin.

By way of example, mention may be made in particular of uricase extracted from boar liver, uricase from *Arthrobacter globiformis*, as well as uricase from *Aspergillus flavus*.

The 2-electron oxidoreductase(s) can be used in pure crystalline form or in a form diluted in a diluent which is inert with respect to the said 2-electron oxidoreductase.

The 2-electron oxidoreductase(s) in accordance with the invention preferably represent(s) from 0.01 to 20% by weight approximately relative to the total weight of the composition, and even more preferably from 0.1 to 5% by weight approximately relative to this weight.

According to the invention, the term donor is understood to refer to the various substrates also necessary for the functioning of the said 2-electron oxidoreductase(s). The nature of the donor (or substrate) for the said enzyme varies depending on the nature of the 2-electron oxidoreductase used. For example, as donors for the pyranose oxidases, mention may be made of D-glucose, L-sorbose and D-xylose; as a donor for the glucose oxidases, mention may be made of D-glucose; as donors for the glycerol oxidases, mention may be made of glycerol and dihydroxyacetone; as donors for the lactate oxidases, mention may be made of lactic acid and its salts; as donors for the pyruvate oxidases, mention may be made of pyruvic acid and its salts; and lastly, as donors for the uricases, mention may be made of uric acid and its salts.

The donor(s) (or substrate(s)) used in accordance with the invention preferably represent(s) from 0.01 to 20% by weight approximately relative to the total weight of the composition in accordance with the invention, and even more preferably from 0.1 to 5% approximately relative to this weight.

According to the invention, the term fatty sucronamides (or fatty sucramides) is understood to refer to compounds containing at least one amide function and including at least one sugar portion or sugar derivative and at least one fatty chain; such compounds can, for example, result from the action of a fatty acid or a fatty acid derivative on the amine function of an amino sugar, or from the action of a fatty amine on a sugar containing a carboxylic acid function (free or in lactone form) or a carboxylic acid derivative or alternatively a carbonyl function, this optionally being in the presence of suitable co-reagents. The nonionic fatty sucronamides (or fatty sucramides) in accordance with the invention are preferably chosen from N-substituted aldonamides and polyhydroxylated fatty acid amides or mixtures thereof.

The N-substituted aldonamides which can be used according to the invention may be chosen from those described in patent application EP-A-550,106, the content of which forms an integral part of the present description. Among these, mention may be made of:
 N-substituted lactobionamides, N-substituted maltobionamides, N-substituted cellobionamides, N-substituted mellibionamides and N-substituted gentiobionamides such as:
  (i) N-alkyl lactobionamides, N-alkyl maltobionamides, N-alkyl cellobionamides, N-alkyl mellibionamides or N-alkyl gentiobionamides which are mono- or disubstituted with a linear or branched, saturated or unsaturated aliphatic hydrocarbon-based group which can contain hetero atoms, preferably having up to 36 carbon atoms, more preferably up to 24 carbon atoms and even more particularly from 8 to 18 carbon atoms (for example methyl, ethyl, amyl, hexyl, heptyl, nonyl, decyl, undecyl, dodecyl, tridecyl, tetradecyl, pentadecyl, hexadecyl, heptadecyl, octadecyl; allyl, undecenyl, oleyl, linoleyl, propenyl, heptenyl), with an aromatic hydrocarbon-based group (for example benzyl, aniline, substituted benzyl, phenylethyl, phenoxyethyl, vinylbenzyl) or cycloaliphatic groups (for example cyclopentyl, cyclohexyl);
  (ii) N-lactobionyl amino acid esters, in which the amino acid can be, in particular, alanine, valine, glycine, lysine, leucine, arginine, aspartic acid, glutamic acid, threonine, serine, cysteine, histidine, tyrosine or methionine or can be chosen, for example, from β-alanine, sarcosine, γ-aminobutyric acid, ornithine, citruline or equivalents thereof; the said N-lactobionyl amino acid esters being monosubstituted with a group of formula:

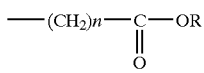

in which R is an aliphatic hydrocarbon-based group which can contain up to 36 carbon atoms and n is an integer greater than 1, as well as the corresponding N-maltobionyl amino acid esters, N-mellibionyl amino acid esters, N-cellobionyl amino acid esters and N-gentiobionyl amino acid esters;

(iii) N-(alkyloxy)alkyl-lactobionamides which are mono- or disubstituted with a group—$(CH_2)_nOR'$ in which R' is an aliphatic, aromatic or cycloaliphatic hydrocarbon-based group as defined in paragraph (i);

(iv) N-(polyalkyloxy)alkyl lactobionamides, N-(polyalkyloxy)alkyl maltobionamides, N-(polyalkyloxy)alkyl cellobionamides, N-(polyalkyloxy)alkyl mellibionamides or N-(polyalkyloxy)alkyl gentiobionamides which are mono- or disubstituted with a group —$R_1$—$(OR_1)_nR_1R_2$ in which $R_1$ is an alkylene group such as ethylene, propylene or mixtures thereof, n is an integer greater than 1, $R_2$ is a lactobionamide, maltobionamide, cellobionamide, mellibionamide or gentiobionamide group.

The polyhydroxylated fatty amides in accordance with the present invention are preferably chosen from those described in patent EP-B-550,656, the content of which forms an integral part of the description, and corresponding to the following formula:

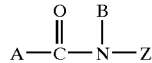

in which B denotes hydrogen, a $C_1$–$C_4$ hydrocarbon-based radical, 2-hydroxyethyl or 2-hydroxypropyl or mixtures thereof, preferably a $C_1$–$C_4$ alkyl such as methyl, ethyl, propyl, isopropyl or n-butyl, and more particularly methyl;

A denotes a $C_5$–$C_{31}$ hydrocarbon-based group, preferably a $C_7$–$C_{15}$ linear alkyl or alkenyl chain or mixtures thereof;

Z denotes a polyhydroxy hydrocarbon-based group having a linear hydrocarbon-based chain with at least 3 hydroxyl groups directly attached to the chain or an alkoxy derivative of the said group (preferably ethoxy or propoxy);

Z is preferably a reducing sugar derivative obtained by reductive amination reaction, and more preferably a glycityl group. Among the reducing sugars, mention may be made of glucose, maltose, lactose, galactose, mannose and xylose.

Even more preferably, Z is chosen from the groups of the following formulae:

—$CH_2$—$(CHOH)_n$—$CH_2OH$;

—$CH$—$(CH_2OH)$—$(CHOH)_{n-1}$—$CH_2OH$;

—$CH_2$—$(CHOH)_2(CHOR')(CHOH)$—$CH_2OH$ in which n is an integer from 3 to 5 and R' is hydrogen or a cyclic or aliphatic monosaccharide and one of the alkoxy derivatives thereof, and among which, the group further preferred is a glycityl group in which n is equal to 4, and in particular the —$CH_2$—$(CHOH)_4$—$CH_2OH$ group.

The group A-CON∠ can be, for example, cocamide, stearamide, oleamide, lauramide, myristyramide, capricamide, palmitamide or tallow amide.

The compositions in accordance with the invention contain the nonionic fatty sucronamides defined above at weight contents which can be between 0.05% and 20%, preferably between 0.1% and 10% and even more preferably between 0.2% and 8%, relative to the total weight of the composition.

A subject of the present invention is also a ready-to-use composition for the oxidation dyeing of keratin fibres, and in particular human keratin fibres such as the hair, of the type comprising, in a medium which is suitable for dyeing, at least one base and, where appropriate, one or more couplers, which is characterized in that it contains:

(a) at least one enzyme of 2-electron oxidoreductase type in the presence of at least one donor for the said enzyme, (b) at least one nonionic fatty sucronamide.

The nature of the oxidation base(s) used in the ready-to-use dye composition is not a critical factor. They can be chosen, in particular, from para-phenylenediamines, double bases, para-aminophenols, ortho-aminophenols and heterocyclic oxidation bases.

Among the para-phenylenediamines which can be used as oxidation bases in the dye compositions in accordance with the invention, mention may be made in particular of the compounds of formula (I, below, and the addition salts thereof with an acid:

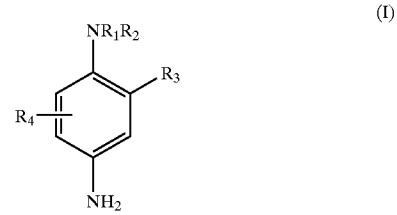

(I)

in which:

$R_1$ represents a hydrogen atom, a $C_1$–$C_4$ alkyl radical, a $C_1$–$C_4$ monohydroxyalkyl radical, a $C_2$–$C_4$ polyhydroxyalkyl radical, a $(C_1$–$C_4)$alkoxy$(C_1$–$C_4)$alkyl radical, a $C_1$–$C_4$ alkyl radical substituted with a nitrogenous group, a phenyl radical or a 4'-aminophenyl radical;

$R_2$ represents a hydrogen atom, a $C_1$–$C_4$ alkyl radical, a $C_1$–$C_4$ monohydroxyalkyl radical, a $C_2$–$C_4$ polyhydroxyalkyl radical, a $(C_1$–$C_4)$alkoxy$(C_1$–$C_4)$alkyl radical or a $C_1$–$C_4$ alkyl radical substituted with a nitrogenous group;

$R_3$ represents a hydrogen atom, a halogen atom such as a chlorine, bromine, iodine or fluorine atom, a $C_1$–$C_4$ alkyl radical, a $C_1$–$C_4$ monohydroxyalkyl radical, a $C_1$–$C_4$ hydroxyalkoxy radical, an acetylamino$(C_1$–$C_4)$ alkoxy radical, a $C_1$–$C_4$ mesylaminoalkoxy radical or a carbamoylamino$(C_1$–$C_4)$alkoxy radical, $R_4$ represents a hydrogen or halogen atom or a $C_1$–$C_4$ alkyl radical.

Among the nitrogenous groups of formula (I) above, mention may be made in particular of amino, mono$(C_1$–$C_4)$ alkylamino, di$(C_1$–$C_4)$alkylamino, tri$(C_1$–$C_4)$alkylamino, monohydroxy$(C_1$–$C_4)$alkylamino, imidazolinium and ammonium radicals.

Among the para-phenylenediamines of formula (I) above, mention may be made more particularly of para-phenylenediamine, para-toluylenediamine, 2-chloro-paraphenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N-(β-methoxyethyl)-para-phenylenediamine, and the addition salts thereof with an acid.

Among the para-phenylenediamines of formula (I) above, para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine and the addition salts thereof with an acid are most particularly preferred.

According to the invention, the term double bases is understood to refer to the compounds containing at least two aromatic rings bearing amino and/or hydroxyl groups.

Among the double bases which can be used as oxidation bases in the dye compositions in accordance with the invention, mention may be made in particular of the compounds corresponding to formula (II) below, and the addition salts thereof with an acid:

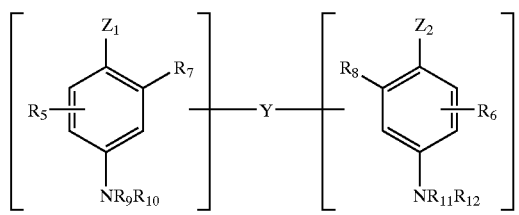

(II)

in which:
Z₁ and Z₂, which may be identical or different, represent a hydroxyl or —NH₂ radical which may be substituted with a $C_1$–$C_4$ alkyl radical or with a linker arm Y;
the linker arm Y represents a linear or branched alkylene chain containing from 1 to 14 carbon atoms, which may be interrupted by or terminated with one or more nitrogenous groups and/or one or more hetero atoms such as oxygen, sulphur or nitrogen atoms, and optionally substituted with one or more hydroxyl or $C_1$–$C_6$ alkoxy radicals;
$R_5$ and $R_6$ represent a hydrogen or halogen atom, a $C_1$–$C_4$ alkyl radical, a $C_1$–$C_4$ monohydroxyalkyl radical, a $C_2$–$C_4$ polyhydroxyalkyl radical, a $C_1$–$C_4$ aminoalkyl radical or a linker arm Y;
$R_7$, $R_8$, $R_9$, $R_{10}$, $R_{11}$ and $R_{12}$, which may be identical or different, represent a hydrogen atom, a linker arm Y or a $C_1$–$C_4$ alkyl radical;

it being understood that the compounds of formula (II) contain only one linker arm Y per molecule.

Among the nitrogenous groups of formula (II) above, mention may be made in particular of amino, mono($C_1$–$C_4$) alkylamino, di($C_1$–$C_4$)alkylamino, tri($C_1$–$C_4$)alkylamino, monohydroxy($C_1$–$C_4$)alkylamino, imidazolinium and ammonium radicals.

Among the double bases of formula (II) above, mention may be made more particularly of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the addition salts thereof with an acid.

Among these double bases of formula (II), N,N'-bis(β-hydroxyethyl)-N,N'-bis(4'-aminophenyl)-1,3-diaminopropanol and 1,8-bis(2,5-diaminophenoxy)-3,5-dioxaoctane, or one of the addition salts thereof with an acid, are particularly preferred.

Among the para-aminophenols which can be used as oxidation bases in the dye compositions in accordance with the invention, mention may be made in particular of the compounds corresponding to formula (III) below, and the addition salts thereof with an acid:

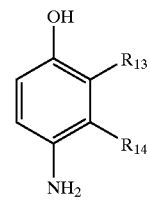

in which:
$R_{13}$ represents a hydrogen or halogen atom or a $C_1$–$C_4$ alkyl, $C_1$–$C_4$ monohydroxyalkyl, ($C_1$–$C_4$)alkoxy ($C_1$–$C_4$)alkyl, $C_1$–$C_4$ aminoalkyl or hydroxy($C_1$–$C_4$) alkylamino-($C_1$–$C_4$)alkyl radical,
$R_{14}$ represents a hydrogen or halogen atom or a $C_1$–$C_4$-alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or ($C_1$–$C_4$)alkoxy($C_1$–$C_4$)alkyl radical,
it being understood that at least one of the radicals $R_{13}$ or $R_{14}$ represents a hydrogen atom.

Among the para-aminophenols of formula (III) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols which can be used as oxidation bases in the dye compositions in accordance with the invention, mention may be made more particularly of 2-aminophenol, 2-amino-5-methylphenol, 2-amino-6-methylphenol and 5-acetamido-2-aminophenol, and the addition salts thereof with an acid.

Among the heterocyclic bases which can be used as oxidation bases in the dye compositions in accordance with the invention, mention may be made more particularly of pyridine derivatives, pyrimidine derivatives, pyrazole derivatives and pyrazolopyrimidine derivatives, and the addition salts thereof with an acid.

Among the pyridine derivatives, mention may be made more particularly of the compounds described, for example, in patents GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives, mention may be made more particularly of the compounds described, for example, in German patent DE 2,359,399 or Japanese patent JP 88-169,571 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof with an acid.

Among the pyrazole derivatives, mention may be made more particularly of the compounds described in patents DE 3,843,892, DE 4,133,957 and patent applications WO 94/08969, WO 94/08970, FR-A-2,733,749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

Among the pyrazolopyrimidine derivatives, mention may be made more particularly of the pyrazolo[1,5-a]pyrimidines of formula (IV) below, and the addition salts thereof with an acid or with a base and the tautomeric forms thereof, when a tautomeric equilibrium exists:

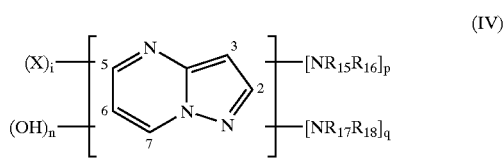

in which:
R$_{15}$, R$_{16}$, R$_{17}$ and R$_{18}$, which may be identical or different, denote a hydrogen atom, a C$_1$–C$_4$ alkyl radical, an aryl radial, a C$_1$–C$_4$ hydroxyalkyl radical, a C$_2$–C$_4$ polyhydroxyalkyl radical, a (C$_1$–C$_4$)alkoxy(C$_1$–C$_4$)alkyl radical, a C$_1$–C$_4$ aminoalkyl radical (it being possible for the amine to be protected with an acetyl, ureido or sulphonyl radical), a (C$_1$–C$_4$)alkylamino(C$_1$–C$_4$)alkyl radical, a di[(C$_1$–C$_4$)alkyl]amino(C$_1$–C$_4$)alkyl radical (it being possible for the dialkyl radicals to form a 5- or 6-membered carbon-based ring or a heterocycle), a hydroxy(C$_1$–C$_4$)alkyl- or di[hydroxy(C$_1$–C$_4$)alkyl] amino(C$_1$–C$_4$)alkyl radical;

the radicals X, which may be identical or different, denote a hydrogen atom, a C$_1$–C$_4$ alkyl radical, an aryl radical, a C$_1$–C$_4$ hydroxyalkyl radical, a C$_2$–C$_4$ polyhydroxyalkyl radical, a C$_1$–C$_4$ aminoalkyl radical, a (C$_1$–C$_4$) alkylamino(C$_1$–C$_4$)alkyl radical, a di[(C$_1$–C$_4$)alkyl] amino(C$_1$–C$_4$)alkyl radical (it being possible for the dialkyls to form a 5- or 6-membered carbon-based ring or a heterocycle), a hydroxy(C$_1$–C$_4$)alkyl- or di[hydroxy(C$_1$–C$_4$)alkyl]amino(C$_1$–C$_4$)alkyl radical, an amino radical, a (C$_1$–C$_4$)alkyl- or di[(C$_1$–C$_4$)alkyl] amino radical; a halogen atom, a carboxylic acid group or a sulphonic acid group;

i is equal to 0, 1, 2 or 3;

p is equal to 0 or 1;

q is equal to 0 or 1;

n is equal to 0 or 1;

with the proviso that:
the sum p+q is other than 0;
when p+q is equal to 2, then n is equal to 0 and the groups NR$_{15}$R$_{16}$ and NR$_{17}$R$_{18}$ occupy the (2,3); (5,6); (6,7); (3,5) or (3,7) positions;
when p+q is equal to 1, then n is equal to 1 and the group NR$_{15}$R$_{16}$ (or NR$_{17}$R$_{18}$) and the OH group occupy the (2,3); (5,6); (6,7); (3,5) or (3,7) positions.

When the pyrazolo[1,5-a]pyrimidines of formula (IV) above are such that they contain a hydroxyl group on one of the positions 2, 5 or 7 α to a nitrogen atom, a tautomeric equilibrium exists represented, for example, by the following scheme:

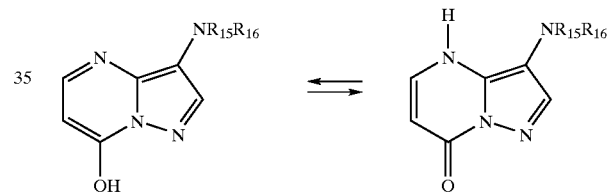

Among the pyrazolo[1,5-a]pyrimidines of formula (IV) above, mention may be made in particular of:
pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)-(2-hydroxyethyl)amino]ethanol;
2-[(7-aminopyrazolo[1,5-a]pyrimidin-3-yl)-(2-hydroxyethyl)amino]ethanol;
5,6-dimethylpyrazolo[1,5-a]pyrimidine-3,7-diamine;
2,6-dimethylpyrazolo[1,5-a]pyrimidine-3,7-diamine;
2,5,N7,N7-tetramethylpyrazolo[1,5-a]pyrimidine-3,7-diamine;
and the addition salts thereof and the tautomeric forms thereof, when a tautomeric equilibrium exists.

The pyrazolo[1,5-a]pyrimidines of formula (IV) above can be prepared by cyclization starting with an aminopyrazole, according to the syntheses described in the following references:

EP 628559 Beiersdorf-Lilly.

R. Vishdu, H. Navedul, Indian J. Chem., 34b (6), 514, 1995.

N. S. Ibrahim, K. U. Sadek, F. A. Abdel-Al, Arch. Pharm., 320, 240, 1987.

R. H. Springer, M. B. Scholten, D. E. O'Brien, T. Novinson, J. P. Miller, R. K. Robins, J. Med. Chem., 25, 235, 1982.

T. Novinson, R. K. Robins, T. R. Matthews, J. Med. Chem., 20, 296, 1977.

U.S. Pat. No. 3,907,799 ICN Pharmaceuticals.

The pyrazolo[1,5-a]pyrimidines of formula (IV) above can also be prepared by cyclization starting from hydrazine, according to the syntheses described in the following references:

A. McKillop and R. J. Kobilecki, Heterocycles, 6(9), 1355, 1977.

E. Alcade, J. De Mendoza, J. M. Marcia-Marquina, C. Almera, J. Elguero, J. Heterocyclic Chem., 11(3), 423, 1974.

K. Saito, I. Hori, M. Higarashi, H. Midorikawa, Bull. Chem. Soc. Japan, 47(2), 476, 1974.

The oxidation base(s) in accordance with the invention preferably represent(s) from 0.0005 to 12% by weight approximately relative to the total weight of the ready-to-use dye composition, and even more preferably from 0.005 to 6% by weight approximately relative to this weight.

The couplers which can be used are those used conventionally in oxidation dye compositions, i.e. meta-phenylenediamines, meta-aminophenols and meta-diphenols, mono- or polyhydroxylated naphthalene derivatives, sesamol and its derivatives and heterocyclic compounds such as, for example, indole derivatives, indoline derivatives, benzimidazole derivatives, benzomorpholine derivatives, sesamol derivatives, pyrazoloazole derivatives, pyrroloazole derivatives, imidazoloazole derivatives, pyrazolopyrimidine derivatives, pyrazoline-3,5-dione derivatives, pyrrolo[3,2-d]oxazole derivatives, pyrazolo[3,4-d]thiazole derivatives, thiazoloazole S-oxide derivatives and thiazoloazole S,S-dioxide derivatives, and the addition salts thereof with an acid.

These couplers can be chosen in particular from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one, and the addition salts thereof with an acid.

When they are present, these couplers preferably represent from 0.0001 to 10% by weight approximately relative to the total weight of the ready-to-use dye composition, and even more preferably from 0.005 to 5% by weight approximately relative to this weight.

In general, the addition salts with an acid which can be used in the context of the dye compositions of the invention (oxidation bases and couplers) are chosen in particular from the hydrochlorides, hydrobromides, sulphates, tartrates, lactates and acetates.

The dye composition of the invention can also contain, in addition to the oxidation dye precursors defined above and the optional combined couplers, direct dyes to enrich the shades with glints. These direct dyes can then be chosen in particular from nitro dyes, azo dyes or anthraquinone dyes.

The subject of the invention is also a process for dyeing keratin fibres, and in particular human keratin fibres such as the hair, using the ready-to-use dye composition as defined above.

According to this process, at least one ready-to-use dye composition as defined above is applied to the fibres, for a period which is sufficient to develop the desired coloration, after which the fibres are rinsed, optionally washed with shampoo, rinsed again and dried.

The time required to develop the coloration on the keratin fibres is generally between 3 and 60 minutes and even more precisely between 5 and 40 minutes.

According to one specific embodiment of the invention, the process includes a first step which consists in separately storing, on the one hand, a composition (A) comprising, in a medium which is suitable for dyeing, at least one oxidation base and optionally at least one coupler as defined above, and, on the other hand, a composition (B) containing, in a medium which is suitable for keratin fibres, at least one enzyme of 2-electron oxidoreductase type in the presence of at least one donor for the said enzyme and at least one nonionic fatty sucronamide as defined above, and then in mixing them together at the time of use, before applying this mixture to the keratin fibres.

According to another specific embodiment of the invention, the fatty nonionic sucronamide is incorporated into composition (A).

According to another specific embodiment of the invention, a composition (A) comprising in a medium which is suitable for dyeing, at least one oxidation base and optionally at least one coupler as defined above, and, on the other hand, a composition (B) containing, in a medium which is suitable for keratin fibres, at least one enzyme of 2-electron oxidoreductase type in the presence of at least one donor for the said enzyme as defined above are stored separately, they are then mixed together at the time of use, after which this mixture is applied to the keratin fibres; composition (A) or composition (B) containing the nonionic fatty sucronamide as defined above.

Another subject of the invention is a multi-compartment dyeing device or "kit" or any other multi-compartment packaging system, a first compartment of which contains composition (A) as defined above and a second compartment of which contains composition (B) as defined above. These devices can be equipped with means for applying the desired mixture to the hair, such as the devices described in patent FR-2,586,913 in the name of the Applicant.

A subject of the present invention is also a novel process for treating keratin substances, in particular the hair, in order to obtain a permanent reshaping of this hair, in particular in the form of permanent-waved hair, this process comprising the following steps: (i) a reducing composition is applied to the keratin substance to be treated, the keratin substance being placed under mechanical tension before, during or after the said application, (ii) the keratin substance is optionally rinsed, (iii) an oxidizing composition as defined above is applied to the optionally rinsed keratin substance, (iv) the keratin substance is optionally rinsed again.

The first step (i) of this process consists in applying a reducing composition to the hair. This application is carried out lock by lock or all at once.

The reducing composition comprises, for example, at least one reducing agent, which can be chosen in particular from thioglycolic acid, cysteine, cysteamine, glyceryl thioglycolate, thiolactic acid or thiolactic or thioglycolic acid salts.

The usual step for placing the hair under tension in a shape corresponding to the desired final shape for this hair (for example curls) can be carried out by any suitable means, in particular mechanical means, which are suitable and known per se for maintaining the hair under tension, such as, for example, rollers, curlers and the like.

The hair can also be shaped without the aid of external means, simply with the fingers.

Before carrying out the following optional rinsing step (ii), the hair onto which the reducing composition has been applied should, conventionally, be left to stand for a few minutes, generally between 5 minutes and one hour, preferably between 10 and 30 minutes, so as to give the reducing agent enough time to act correctly on the hair. This waiting phase preferably takes place at a temperature ranging from 35° C. to 45° C., while preferably also protecting the hair with a hood.

In the optional second step of the process (step (ii)), the hair impregnated with the reducing composition is then rinsed thoroughly with an aqueous composition.

Next, in a third step (step (iii)), the oxidizing composition of the invention is applied to the hair thus rinsed, with the aim of fixing the new shape given to the hair.

As in the case of the application of the reducing composition, the hair onto which the oxidizing composition has been applied s then, conventionally, left for a standing or waiting phase lasting a few minutes, generally between 3 and 30 minutes, preferably between 5 and 15 minutes.

If the hair was maintained under tension by external means, these means (rollers, curlers or the like) can be removed from the hair before or after the fixing step.

Lastly, in the final step of the process according to the invention (step (iv)), which is also optional, the hair impregnated with the oxidizing composition is rinsed thoroughly, generally with water.

Hair which is soft and easy to disentangle is finally obtained. The hair is wavy.

The oxidizing composition according to the invention can also be used in a process for bleaching keratin fibres, and in particular the hair.

The bleaching process according to the invention comprises a step of applying an oxidizing composition according to the invention to the keratin fibres in the presence or absence of an auxiliary oxidizing agent. Conventionally, a second step of the bleaching process according to the invention is a step of rinsing the keratin fibres.

The medium which is suitable for the keratin fibres (or the support) for the ready-to-use dye compositions and for the oxidizing compositions used for the permanent reshaping or bleaching of keratin fibres in accordance with the invention generally consists of water or of a mixture of water and at least one organic solvent in order to dissolve the compounds which would not be sufficiently soluble in water. By way of organic solvent, mention may be made, for example, of $C_1$–$C_4$ alkanols such as ethanol and isopropanol; glycerol; glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents can be present in proportions preferably of between 1 and 40% by weight approximately relative to the total weight of the dye composition, and even more preferably between 5 and 30% by weight approximately.

The pH of the ready-to-use dye compositions and of the oxidizing compositions used for the permanent reshaping or bleaching of the keratin fibres in accordance with the invention is chosen such that the enzymatic activity of the 2-electron oxidoreductase is not adversely affected. It is generally between 5 and 11 approximately, and preferably between 6.5 and 10 approximately. It can be adjusted to the desired value using acidifying or basifying agents usually used for dyeing keratin fibres.

Among the acidifying agents, mention may be made, by way of example, of inorganic or organic acids such as hydrochloric acid, orthophosphoric acid, sulphuric acid, carboxylic acids such as acetic acid, tartaric acid, citric acid or lactic acid, and sulphonic acids.

Among the basifying agents, mention may be made, by way of example, of aqueous ammonia, alkaline carbonates, alkanolamines such as mono-, di- and triethanolamines, 2-methyl-2-aminopropanol and derivatives thereof, sodium hydroxide, potassium hydroxide and the compounds of formula (V) below:

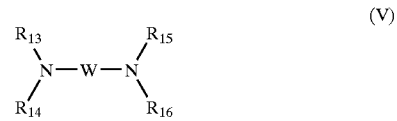

in which W is a propylene residue optionally substituted with a hydroxyl group or a $C_1$–$C_4$ alkyl radical; $R_{13}$, $R_{14}$, $R_{15}$ and $R_{16}$, which may be identical or different, represent a hydrogen atom or a $C_1$–$C_4$ alkyl or $C_1$–$C_4$ hydroxyalkyl radical.

The ready-to-use dye compositions and the oxidizing compositions for the permanent reshaping or bleaching of keratin fibres in accordance with the invention can also contain various adjuvants used conventionally in compositions for dyeing, permanently reshaping or bleaching the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, enzymes other than the 2-electron oxidoreductases used in accordance with the invention, such as, for example, peroxidases, penetration agents, sequestering agents, fragrances, buffers, dispersing agents, conditioners, film-forming agents, preserving agents and opacifiers.

Needless to say, a person skilled in the art will take care to select this or these optional complementary compound(s) such that the advantageous properties intrinsically associated with the compositions in accordance with the invention are not, or are not substantially, adversely affected by the addition or additions envisaged.

The ready-to-use dye compositions and the oxidizing compositions used for the permanent reshaping or bleaching of keratin fibres in accordance with the invention can be in various forms, such as in the form of liquids, creams or gels, which are optionally pressurized, or in any other form which is suitable for dyeing, permanently reshaping or bleaching keratin fibres, and in particular human hair.

In the case of a ready-to-use dye composition, the oxidation dyes(s) and the 2-electron oxidoreductase(s) are present in the said composition, which must be free of oxygen gas, so as to avoid any premature oxidation of the oxidation dye(s).

Concrete examples illustrating the invention will now be given.

In the text hereinabove and hereinbelow, except where otherwise mentioned, the percentages are expressed on a weight basis.

The examples which follow illustrate the invention without being limiting in nature.

EXAMPLES 1 AND 2

Dye Compositions

The ready-to-use dye compositions below were prepared (contents in grams):

Example 1

| | |
|---|---|
| Uricase from *Arthrobacter globiformis* at a concentration of 20 International Units (I.U.)/mg, sold by the company Sigma | 1.5 g |
| Uric acid | 1.5 g |
| Ethanol | 20.0 g |
| Hydroxyethylcellulose sold under the name Natrosol 250 HHR by the company Aqualon | 1.0 g |
| N-Cocolactobionamide | 5.0 g |
| Para-Phenylenediamine | 0.324 g |
| Resorcinol | 0.33 g |
| Demineralized water | qs 100 g |

Example 2

| | |
|---|---|
| Uricase from *Arthrobacter globiformis* at a concentration of 20 International Units (I.U.)/mg, sold by the company Sigma | 1.5 g |
| Uric acid | 1.5 g |
| Ethanol | 20.0 g |
| Hydroxyethylcellulose sold under the name Natrosol 250 HHR by the company Aqualon | 1.0 g |
| N-Decanoyl-N-methylglucamine [polyhydroxylated fatty acid amide of formula: $C_9H_{19}$—CO—N(CH$_3$)—CH$_2$—(CHOH)$_4$—CH$_2$OH] | 5 g |
| Para-Phenylenediamine | 0.324 g |
| Resorcinol | 0.33 g |
| Demineralized water | qs 100 g |

Each of the ready-to-use dye compositions desribed above was applied to locks of natural grey hair containing 90% white hairs for 30 minutes. The hair was then rinsed, washed with a standard shampoo and then dried.

Locks of hair dyed a matt dark-blonde colour were obtained with each dye composition.

Example 3

Oxidizing Composition for Permanent-waving or Bleaching

| | |
|---|---|
| Uricase from *Arthrobacter globiformis* at a concentration of 20 International Units (I.U.)/mg, sold by the company Sigma | 1.8 |
| Uric acid | 1.65 |
| Ethanol | 20.0 |
| N-Octanoyl-N-methylglucamine [polyhydroxylated fatty acid amide of formula: $C_7H_{15}$—CO—N(CH$_3$)—CH$_2$—(CHOH)$_4$—CH$_2$OH] | 5 g |
| 2-Methyl-2-amino-1-propanol | 5 g |
| | qs pH 9.5 |
| Distilled water | qs 100 g |

What is claimed is:

1. A cosmetic or dermatological composition for treating keratin fibers comprising:
   (a) at least one enzyme chosen from 2-electron oxidoreductases,
   (b) at least one donor for said at least one enzyme, and
   (c) at least one nonionic fatty sucronamide.

2. The composition according to claim 1, wherein said keratin fibers are human keratin fibers.

3. The composition according to claim 2, wherein said human keratin fibers are hair.

4. The composition according to claim 1, wherein said at least one enzyme is chosen from pyranose oxidases, glucose oxidases, glycerol oxidases, lactate oxidases, pyruvate oxidases, and uricases.

5. The composition according to claim 1, wherein said at least one enzyme is chosen from uricases of animal, microbiological and biotechnological origin.

6. The composition according to claim 1, wherein said at least one enzyme is present in an amount ranging from 0.01 to 20% by weight relative to the total weight of the composition.

7. The composition according to claim 6, wherein said at least one enzyme is present in an amount ranging from 0.1 to 5% by weight relative to the total weight of the composition.

8. The composition according to claim 1, wherein said at least one donor is chosen from D-glucose, L-sorbose, D-xylose, glycerol, dihydroxyacetone, lactic acid and its salts, pyruvic acid and its salts, and uric acid and its salts.

9. The composition according to claim 8, wherein said at least one donor is chosen from uric acid and its salts.

10. The composition according to claim 1, wherein said at least one donor is present in an amount ranging from 0.01 to 20% by weight relative to the total weight of the composition.

11. The composition according to claim 10, wherein said at least one donor is present in an amount ranging from 0.1 to 5% by weight relative to the total weight of the composition.

12. The composition according to claim 1, wherein said at least one nonionic fatty sucronamide is chosen from N-substituted aldonamides and polyhydroxylated fatty acid amides.

13. The composition according to claim 12, wherein said N-substituted aldonamides are chosen from:
   (i) N-alkyl lactobionamides, N-alkyl maltobionamides, N-alkyl cellobionamides, N-alkyl mellibionamides and N-alkyl gentiobionamides which are monosubstituted or disubstituted with groups chosen from linear and branched, saturated and unsaturated aliphatic hydrocarbon-based groups, aromatic hydrocarbon-based groups, and cycloaliphatic groups;
   (ii) amino acid esters chosen from N-lactobionyl, N-maltobionyl, N-mellibionyl, N-cellobionyl, and N-gentiobionyl amino acid esters, wherein the amino acid is chosen from alanine, valine, glycine, lysine, leucine, arginine, aspartic acid, glutamic acid, threonine, serine, cysteine, histidine, tyrosine, methionine, β-alanine, sarcosine, γ-aminobutyric acid, ornithine, and citruline, said amino acid esters being monosubstituted with groups of formula:

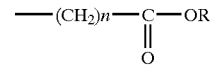

wherein R is chosen from aliphatic hydrocarbon-based groups which comprise from 1 to 36 carbon atoms and n is an integer greater than 1;
   (iii) N-(alkyloxy)alkyl-lactobionamides which are monosubstituted or disubstituted with groups —(CH$_2$)$_n$OR' wherein n is an integer greater than 1 and R' is chosen from linear and branched, saturated and unsaturated aliphatic hydrocarbon-based groups, aromatic hydrocarbon-based groups, and cycloaliphatic groups;

(iv) N-(polyalkyloxy)alkyl lactobionamides, N-(polyalkyloxy)alkyl maltobionamides, N-(polyalkyloxy)alkyl cellobionamides, N-(polyalkyloxy)alkyl mellibionamides and N-(polyalkyloxy)alkyl gentiobionamides which are monosubstituted or disubstituted with groups —R$_1$—(OR$_1$)$_n$R$_1$R$_2$ wherein R$_1$ is chosen from alkylene groups, n is an integer greater than 1, and R$_2$ is chosen from lactobionamides, maltobionamides, cellobionamides, mellibionamides and gentiobionamides.

14. The composition according to claim 13, wherein said aliphatic hydrocarbon-based groups comprise from 1 to 36 carbon atoms.

15. The composition according to claim 14, wherein said aliphatic hydrocarbon-based groups comprise from 1 to 24 carbon atoms.

16. The composition according to claim 15, wherein said aliphatic hydrocarbon-based groups comprise from 8 to 18 carbon atoms.

17. The composition according to claim 13, wherein said aliphatic hydrocarbon-based groups comprise hetero atoms.

18. The composition according to claim 13, wherein said R$_1$ alkylene groups are chosen from ethylene and propylene.

19. The composition according to claim 12, wherein said polyhydroxylated fatty acid amides are chosen from the following formula:

wherein B is chosen from hydrogen, C$_1$–C$_4$ hydrocarbon-based radicals, 2-hydroxyethyl, 2-hydroxypropyl, A is chosen from C$_5$–C$_{31}$ hydrocarbon-based groups, Z is chosen from:
 polyhydroxy hydrocarbon-based groups having at least one linear hydrocarbon-based chain with at least 3 hydroxyl groups directly attached to said chain, and
 alkoxy derivatives of said polyhydroxy hydrocarbon-based groups wherein at least one of said hydroxyl groups is replaced by an alkoxy group.

20. The composition according to claim 19, wherein B is C$_1$–C$_4$ alkyl.

21. The composition according to claim 20, wherein B is methyl.

22. The composition of claim 19, wherein A is chosen from C$_7$–C$_{15}$ linear alkyls and C$_7$–C$_{15}$ linear alkenyls.

23. The composition according to claim 19, wherein Z is chosen from reducing sugar derivatives obtained by reductive amination reactions.

24. The composition according to claim 23, wherein said reducing sugar derivatives are obtained from glucose, maltose, lactose, galactose, mannose and xylose.

25. The composition according to claim 23, wherein Z is a glycityl group.

26. The composition according to claim 19, wherein Z is chosen from:

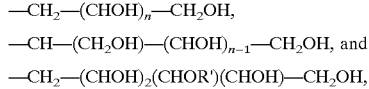

wherein n is an integer from 3 to 5 and R' is chosen from hydrogen atoms, and from cyclic monosaccharides, aliphatic monosaccharides, and alkoxy derivatives thereof wherein, in said derivatives, at least one hydroxy group of said monosaccharides is replaced by an alkoxy group.

27. The composition according to claim 26, wherein Z is

28. The composition according to claim 19, wherein said polyhydroxylated fatty acid amides corresponding to the formula AC(O)N(B)Z are chosen from cocamide, stearamide, oleamide, lauramide, myristyramide, capricamide, palmitamide, and tallow amide.

29. The composition according to claim 1, wherein said at least one nonionic fatty sucronamide is present in an amount ranging from 0.05% to 20% by weight relative to the total weight of the composition.

30. The composition according to claim 29, wherein said at least one nonionic fatty sucronamide is present in an amount ranging from 0.1 to 10% by weight relative to the total weight of the composition.

31. The composition according to claim 1, further comprising water or a mixture of water and at least one organic solvent.

32. The composition according to claim 31, wherein said at least one organic solvent is present in an amount ranging from 1 to 40% by weight relative to the total weight of the composition.

33. The composition according to claim 32, wherein said at least one organic solvent is present in an amount ranging from 5 to 30% by weight relative to the total weight of the composition.

34. The composition according to claim 1, wherein the pH ranges from 5 to 11.

35. The composition according to claim 34, wherein said pH ranges from 6.5 to 10.

36. The composition according to claim 1, further comprising at least one cosmetic adjuvant chosen from anionic, cationic, nonionic, amphoteric and zwitterionic surfactants; anionic, cationic, nonionic, amphoteric and zwitterionic polymers; inorganic and organic thickeners; antioxidants; enzymes other than said 2-electron oxidoreductases; penetration agents; sequestering agents; fragrances; buffers; dispersing agents; conditioners; film-forming agents; preserving agents; and opacifiers.

37. The composition according to claim 1, comprising:
(a) at least one enzyme chosen from 2-electron oxidoreductases chosen from:
 pyranose oxidase, glucose oxidases, glycerol oxidases, lactate oxidases, pyruvate oxidases, and uricases;
(b) at least one donor for said at least one enzyme chosen from:
 D-glucose, L-sorbose, D-xylose, glycerol, dihydroxyacetone, lactic acid and its salts, pyruvic acid and its salts, and uric acid and its salts; and
(c) at least one nonionic fatty sucronamide chosen from:
(1) N-substituted aldonamides chosen from:
 (i) N-alkyl lactobionamides, N-alkyl maltobionamides, N-alkyl cellobionamides, N-alkyl mellibionamides and N-alkyl gentiobionamides; which are monosubstituted or disubstituted with groups chosen from linear and branched, saturated and unsaturated aliphatic hydrocarbon-based groups which may contain heteroatoms, aromatic hydrocarbon-based groups, cycloaliphatic groups;
 (ii) amino acid esters chosen from N-lactobionyl, N-maltobionyl, N-mellibionyl, N-cellobionyl, and N-gentiobionyl amino acid esters, wherein the amino acids are chosen from alanine, valine, glycine, lysine, leucine, arginine, aspartic acid, glutamic acid, threonine, serine, cysteine, histidine, tyrosine, methionine, β-alanine, sarcosine, γ-aminobutyric acid, ornithine, and citruline, said amino acid esters being monosubstituted with groups of formula:

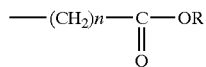

wherein R is chosen from aliphatic hydrocarbon-based groups which comprise from 1 to 36 carbon atoms and n is an integer greater than 1;
(iii) N-(alkyloxy)alkyl-lactobionamides which are monosubstituted or disubstituted with groups —$(CH_2)_nOR'$ wherein n is an integer greater than 1 and R' is chosen from linear and branched, saturated and unsaturated aliphatic hydrocarbon-based groups, aromatic hydrocarbon-based groups, and cycloaliphatic groups; and
(iv) N-(polyalkyloxy)alkyl lactobionamides, N-(polyalkyloxy)alkyl maltobionamides, N-(polyalkyloxy)alkyl cellobionamides, N-(polyalkyloxy)alkyl mellibionamides and N-(polyalkyloxy)alkyl gentiobionamide which are monosubstituted or disubstituted with groups —$R_1$—$(OR_1)_nR_1R_2$ wherein $R_1$ is chosen from alkylene groups, n is an integer greater than 1, and $R_2$ is chosen from lactobionamides, maltobionamides, cellobionamides, mellibionamides and gentiobionamides; and
(2) polyhydroxylated fatty acid amides chosen from compounds of the following formula:

wherein B is chosen from hydrogen, $C_1$–$C_4$ hydrocarbon-based radicals, 2-hydroxyethyl, and 2-hydroxypropyl,
A is chosen from $C_5$–$C_{31}$ hydrocarbon-based groups, and
Z is chosen from:
polyhydroxy hydrocarbon-based groups having at least one linear hydrocarbon-based chain with at least 3 hydroxyl groups directly attached to said chains, and new line alkoxy derivatives of said polyhydroxy hydrocarbon-based groups wherein at least one of said hydroxyl groups is replaced by an alkoxy group.

38. A ready-to-use composition for oxidation dyeing of keratin fibers, comprising:
(a) at least one enzyme chosen from 2-electron oxidoreductases,
(b) at least one donor for said at least one enzyme,
(c) at least one nonionic fatty sucronamide, and
(d) at least one oxidation base.

39. The ready-to-use composition according to claim 38, wherein said at least one oxidation base is chosen from para-phenylenediamines, double bases, ortho-aminophenols, para-aminophenols, heterocyclic bases, and acid-addition salts thereof.

40. The ready-to-use composition according to claim 38, wherein said at least one oxidation base is present in a amount ranging from 0.0005 to 12% by weight relative to the total weight of the composition.

41. The ready-to-use composition of claim 38, further comprising at least one coupler.

42. The ready-to-use composition according to claim 41, wherein said at least one coupler is chosen from meta-phenylenediamines, meta-aminophenols, meta-diphenols, heterocyclic couplers, and acid-addition salts thereof.

43. The ready-to-use composition according to claim 41 wherein said at least one coupler is present in an amount ranging from 0.0001 to 10% by weight relative to the total weight of the composition.

44. The ready-to-use composition according to claim 39, wherein said acid-addition salts are chosen from hydrochloride, hydrobromides, sulphates, tartrates, lactates and acetates.

45. The ready-to-use composition according to claim 42, wherein said acid-addition salts are chosen from hydrochlorides, hydrobromides, sulphates, tartrates, lactates and acetates.

46. The ready-to-use composition according to claim 38, further comprising at least one direct dye.

47. A ready-to-use composition for oxidation dyeing of keratin fibers comprising:
(a) at least one enzyme of 2-electron oxidoreductase type, chosen from pyranose oxidases, glucose oxidases, glycerol oxidases, lactate oxidases, pyruvate oxidases, and uricases; and
(b) at least one donor for said at least one enzyme, chosen from D-glucose, L-sorbose, D-xylose, glycerol, dihydroxyacetone, lactic acid and its salts, pyruvic acid and its salts, and uric acid and its salts;
(c) at least one nonionic fatty sucronamide chosen from:
N-substituted aldonamides chosen from:
(i) N-alkyl lactobionamides N-alkyl maltobionamides N-alkyl cellobionamides, N-alkyl mellibionamides and N-alkyl gentiobionamides; which are monosubstituted or disubstituted with: linear and branched, saturated and unsaturated aliphatic hydrocarbon-based groups which may contain heteroatoms, aromatic hydrocarbon-based groups, and cycloaliphatic groups;
(ii) amino acid esters chosen from N-lactobionyl, N-maltobionyl, N-mellibionyl, N-cellobionyl, and N-gentiobionyl amino acid esters, wherein the amino acids are chosen from alanine, valine, glycine, lysine, leucine, arginine, aspartic acid, glutamic acid, threonine, serine, cysteine, histidine, tyrosine, methionine, β-alanine, sarcosine, y-aminobutyric acid, ornithine, and citruline,
said amino acid esters being monosubstituted with groups of formula:

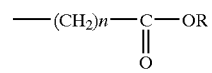

wherein R is chosen from aliphatic hydrocarbon-based groups which comprise from 1 to 36 carbon atoms and n is an integer greater than 1;
(iii) N-(alkyloxy)alkyl-lactobionamides which are mono-substituted or disubstituted with groups —$(CH_2)_nOR'$ wherein n is an integer greater than 1 and R' chosen from linear and branched, saturated and unsaturated aliphatic hydrocarbon-based groups which may contain heteroatoms, aromatic hydrocarbon-based groups, and cycloaliphatic groups;

(iv) N-(polyalkyloxy)alkyl lactobionamides, N-(polyalkyloxy)alkyl maltobionamides, N-(polyalkyloxy)alkyl cellobionamides, N-(polyalkyloxy)alkyl mellibionamides and N-(polyalkyloxy)alkyl gentiobionamides; which are monosubstituted or disubstituted with groups —$R_1$-$(OR_1)_nR_1R_2$ wherein $R_1$ is chosen from alkylene groups, n is an integer greater than 1, and $R_2$, is chosen from lactobionamides, maltobionamides, cellobionamides, mellibionamides and gentiobionamides; and polyhydroxylated fatty acid amides chosen from compounds of the following formula:

wherein B is chosen from hydrogen, $C_1$–$C_4$ hydrocarbon-based radicals, 2-hydroxyethyl, and 2-hydroxypropyl, A is chosen from $C_5$–$C_{31}$ hydrocarbon-based groups, Z is chosen from:

polyhydroxy hydrocarbon-based groups having at least one linear hydrocarbon-based chain with at least 3 hydroxyl groups directly attached to said chains, and alkoxy derivatives of said polyhydroxy hydrocarbon-based groups wherein at least one of said hydroxyl groups is replaced by an alkoxy group: and (c) at east one oxidation base, chosen from para-phenylenediamines chosen from para-phenylenediamine para-toluylenediamine, 2-chloro-para-phenylenediamine, 2,3-dimethyl-para-phenylenediamine, 2,6-dimethyl-para-phenylenediamine, 2,6-dimethyl-para-phenylenediamine, 2,5-dimethyl-para-phenylenediamine N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl))aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine. N,N-dimethyl-3- methyl-para-phenylenediamine, N,N-(ethyl-βhydroxyethyl)-para-phenylenediamine, N-(β,γ-dihydroxypropyl)-para-phenylenediamine, N-(4'- aminophenyl)-para-phenylenediamine, N,N' phenyl-para-phenylenediamine, 2-β- hydroxyethyloxy-para-phenylenediamine, 2-β-acetylaminoethyloxy-para-phenylenediamine and N-(β-methoxyethyl)-para-phenylenediamine, and acid addition salts thereof;

double bases chosen from N,N'-bis(β-hydroxyethyl)-N,N'-bis(4'-amino- phenyl)-1,3-diaminopropanol, N,N'-bis(β-hydroxyethyl)-N,N'-bis(4'-amino- phenyl) ethylenediamine, N,N'-bis(4-aminophenyl) tetramethylenediamine, N,N'-bis(β-hydroxyethyl(4-aminophenyl)tetramethylenediamine. N,N'- bis(4-methylaminophenyl)tetramethylenediamine, N,N'-bis (ethyl)-N,N'-bis(4'- amino-3'-methylphenyl) ethylenediamine, 1,8-bis(2,5-diaminophenoxy)-3,5-dioxaoctane, and acid-addition, salts thereof;

ortho-aminophenols chosen from 2-aminophenol, 2-amino-5- methylphenol, 2-amino-6-methylphenol, 5-acetamido-2-aminophenol, and acid addition salts thereof;

para-aminophenols chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid-addition salts thereof; and heterocyclic bases chosen from pyridine compounds, pyrimidine compounds, pyrazole compounds; pyrazolopyrimidine compounds, and acid addition salts thereof.

48. A ready-to-use composition for oxidation dyeing of keratin fibers comprising: uricase, uric acid, N-cocolactobionamide, para-phenylenediamine, and resorcinol.

49. A ready-to-use composition for oxidation dyeing of keratin fibers comprising: uricase, uric acid, N-decanoyl-N-methylglucamine, para-phenylenediamine, and resorcinol.

50. A process for dyeing keratin fibers, comprising:

applying to said keratin fibers a composition, and developing for a period of time sufficient to achieve a desired coloration, wherein said composition comprises:

(a) at least one enzyme chosen from 2-electron oxidoreductases, (b) at east one donor for said at least one enzyme, and (c) at least one nonionic fatty sucronamide.

51. The process according to claim 50, wherein said keratin fibers are human keratin fibers.

52. The process according to claim 51, wherein said human keratin fibers are hair.

53. A process for dyeing keratin fibers, comprising:

separately storing a first composition, separately storing a second composition, thereafter mixing said first composition with said second composition, applying said mixture to said fibers, and developing for a period of time sufficient to achieve a desired coloration;

wherein said first composition comprises at least one oxidation base;

wherein said second composition comprises at least one enzyme chosen from 2-electron oxidoreductases and at least one donor for said at least one enzyme;

wherein at least one of said first composition and said second composition further comprises at least one nonionic fatty sucronamide.

54. The process according to claim 53, wherein said first composition further comprises at least one coupler.

55. A multi-compartment dyeing kit, comprising at least two separate compartments, wherein a first compartment contains a first composition, and a second compartment contains a second composition;

wherein said first composition comprises at east one oxidation base;

wherein said second composition comprises at least one enzyme chosen from 2-electron oxidoreductases and at least one donor for said at least one enzyme;

wherein at least one of said first composition and said second composition further comprises at least one nonionic fatty sucronamide.

56. A process for obtaining permanent reshaping of keratin fibers, comprising:

applying a reducing composition to said keratin fibers to be re-shaped, said fibers being placed under mechanical tension before, during or after said applying; and applying an oxidizing composition to said fibers;

wherein said oxidizing composition comprises:

at last one enzyme chosen from 2-oxidoreductases, at least one donor for said at least one enzyme, and at least one nonionic fatty sucronamide.

57. The process according to claim 56, wherein said oxidizing composition comprises: uricase, uric acid, and N-octanoyl-N-methylglucamine.

58. The process according to claim 56, further comprising:

rinsing said keratin/fibers after said applying of said reducing composition.

59. The process according to claim 56, further comprising:

rinsing said keratin fibers after said applying of said oxidizing composition.

60. A process for bleaching keratin fibers, comprising:

applying an oxidizing composition to said keratin fibers to be bleached, and thereafter rinsing said keratin fibers, wherein said oxidizing composition comprises:

at least one enzyme chosen from 2-oxidoreductases and at least one donor for said at least one enzyme, and at least one nonionic fatty sucronamide.

61. The process according to claim 60, wherein the oxidizing composition further comprises an auxiliary oxidizing agent.

* * * * *

UNITED STATES PATENT AND TRADEMARK OFFICE
CERTIFICATE OF CORRECTION

PATENT NO. : 6,692,537 B1  
DATED : February 17, 2004  
INVENTOR(S) : Roland de la Mettrie et al.

It is certified that error appears in the above-identified patent and that said Letters Patent is hereby corrected as shown below:

Column 20,  
Lines 2-2, "a amount" should read -- an amount --  
Line 17, "hydrochloride," should read -- hydrochlorides, --.  
Line 38, after "lactobionamides", insert a comma; and after "maltobionamides", insert a comma.  
Line 51, "y-aminobutyric" should read -- γ-aminobutyric --.

Column 21,  
Line 10, after "R$_2$", delete the comma.  
Lines 34-35, after "para-phenylenediamine", insert a comma.  
Lines 38-39, "2,6-dimethyl-para-phenylenediamine," should read  
-- 2,6-diethyl-para-phenylenediamine, --.  
Lines 46-47, "4-amino-2-chloro-N,N-bis(β-hydroxyethyl))aniline,"  
should read -- 4-amino-2-chloro-N,N-bis(β-hydroxyethyl)aniline, --  
Lines 51-52, "2-hydroxymethyl-para-phenylenediamine."  
should read -- 2-hydroxymethyl-para-phenylenediamine, --.  
Lines 52-53, "N,N-dimethyl-3- methyl-para-phenylenediamine,"  
should read -- N,N-dimethyl-3-methyl-para-phenylenediamine, --.  
Lines 53-54, "N,N-(ethyl-βhydroxyethyl)-para-phenylenediamine," should read  
-- N,N-(ethyl-β-hydroxyethyl)-para-phenylenediamine, --.  
Lines 55-56, "N-(4'- aminophenyl)-para-phenylenediamine,"  
should read -- N-(4'-aminophenyl)-para-phenylenediamine, --.  
Lines 56-57, "N,N' phenyl-para-phenylenediamine,"  
should read -- N-phenyl-para-phenylenediamine, --.  
Lines 57-58, "2-β- hydroxyethyloxy-para-phenylenediamine,"  
should read -- 2-β-hydroxyethyloxy-para-phenylenediamine, --.  
Line 60, "acid addition" should read -- acid-addition --.  
Lines 61-62, "N,N'-bis(β-hydroxyethyl)-N,N'-bis(4'-amino- phenyl)-  
1,3-diaminopropanol," should read -- N,N'bis(β-hydroxyethyl)-N,N'-bis(4'-amino-phenyl)- 1,3-diaminopropanol, --.  
Lines 62-64, "N,N'-bis(β-hydroxyethyl)-N,N'-bis(4'-amino-phenyl)ethylenediamine,  
should read -- N,N'-bis(β-hydroxyethyl)-N,N'-bis(4'-amino-phenyl)ethylenediamine, --  
Lines 65-66, "N,N'-bis(β-hydroxyethyl(4-aminophenyl)tetramethylenediamine." should read -- N,N'-bis(β-hydroxyethyl)-N,N-bis(4-aminophenyl)tetramethylenediamine, --.  
Lines 66-67, "N,N'- bis(4-methylaminophenyl)tetramethylenediamine,"  
should read -- N,N'-bis(4-methylaminophenyl)tetramethylenediamine, --.

UNITED STATES PATENT AND TRADEMARK OFFICE
CERTIFICATE OF CORRECTION

PATENT NO.     : 6,692,537 B1
DATED          : February 17, 2004
INVENTOR(S)    : Roland de la Mettrie et al.

It is certified that error appears in the above-identified patent and that said Letters Patent is hereby corrected as shown below:

Column 21, through Column 22,
Lines 67-line 2, "N,N'-bis(ethyl)-N,N'-bis(4'- amino-3'-methylphenyl) ethylenediamine," should read -- N,N'-bis(ethyl)-N,N'-bis(4'-amino-3'-methylpheny)ethylenediamine.

Column 22,
Line 3, after "acid-addition", delete the comma.
Line 5, "2-amino-5- methylphenol," should read -- 2-amino-5-methylphenol, --
Lines 6 and 19, "acid addition" should read -- acid-addition --.
Lines 36 and 66, "at east" should read-- at least --.

Column 23,
Line 10, "re-shaped," should read -- reshaped, --.
Line 15, "at last" should read -- at  least --.

Signed and Sealed this

Eighth Day of June, 2004

JON W. DUDAS
*Acting Director of the United States Patent and Trademark Office*